United States Patent
Fries et al.

(10) Patent No.: US 6,347,040 B1
(45) Date of Patent: Feb. 12, 2002

(54) SENSOR DEVICE FOR SENSING BIOMETRIC CHARACTERISTICS, IN PARTICULAR FINGER MINUTIAE

(75) Inventors: Manfred Fries, Hunderdorf; Reinhard Fischbach, Regensburg; Detlef Houdeau, Langquaid, all of (DE)

(73) Assignee: Infineon Technologies AG, Munich (DE)

( * ) Notice: Subject to any disclaimer, the term of this patent is extended or adjusted under 35 U.S.C. 154(b) by 0 days.

(21) Appl. No.: 09/716,902

(22) Filed: Nov. 20, 2000

Related U.S. Application Data

(63) Continuation of application No. PCT/DE99/01478, filed on May 17, 1999.

(30) Foreign Application Priority Data

May 19, 1998 (DE) .......................................... 198 22 504

(51) Int. Cl.⁷ ................................................. H05K 7/02
(52) U.S. Cl. ....................... 361/760; 361/749; 361/761; 341/20
(58) Field of Search ................................ 361/760, 736, 361/720, 749, 761, 764, 797, 807, 809, 799; 257/669, 675; 174/254, 260, 256, 138 G, 51; 341/27, 20; 324/686; 340/365 C, 365

(56) References Cited

U.S. PATENT DOCUMENTS

| | | | | |
|---|---|---|---|---|
| 4,264,903 A | * | 4/1981 | Bigelow | 340/364 C |
| 4,772,100 A | * | 9/1988 | Suenaga | 350/365 |
| 5,657,012 A | * | 8/1997 | Tait | 341/20 |
| 6,028,773 A | * | 2/2000 | Hundt | 361/760 |

FOREIGN PATENT DOCUMENTS

| | | |
|---|---|---|
| DE | 37 04 870 C1 | 4/1988 |
| EP | 0 786 745 A2 | 7/1997 |
| FR | 2 736 179 A1 | 1/1997 |

* cited by examiner

*Primary Examiner*—Jeffrey Gaffin
*Assistant Examiner*—Hung Bui
(74) *Attorney, Agent, or Firm*—Herbert L. Lerner; Laurence A. Greenberg; Werner H. Stemer

(57) ABSTRACT

The sensor device is provided for sensing biometric characteristics, in particular finger minutiae, with a biometric sensor chip. The sensor chip is fastened on a flexible printed circuit board that has a highly flexible substrate layer and conductor tracks applied to the substrate layer. The conductor tracks are in electrical contact with the sensor chip and are led to a terminal region of the flexible printed circuit board. The sensing area of the sensor chip is accessible through an opening in the flexible circuit board and the opening is at least partially surrounded by a grounding frame.

6 Claims, 2 Drawing Sheets

US 6,347,040 B1

SENSOR DEVICE FOR SENSING BIOMETRIC CHARACTERISTICS, IN PARTICULAR FINGER MINUTIAE

CROSS-REFERENCE TO RELATED APPLICATION

This is a continuation of copending International Application PCT/DE99/01478, filed May 17, 1999, which designated the United States.

BACKGROUND OF THE INVENTION

Field of the Invention

The invention relates to a sensor device for sensing biometric characteristics, in particular finger minutiae, by means of a biometric sensor chip. The sensor chip is fastened on a flexible printed circuit board which comprises a highly flexible substrate layer and conductor tracks that have been applied to the substrate layer, are in electrical contact with the sensor chip, and are led to a terminal region of the flexible printed circuit board.

It has been known heretofore to sense personal characteristics, for example finger minutiae, i.e. fingerprints, by means of biometric fingertip sensors, in order to permit or deny access to an appliance, a room etc. according to the result of the sensing. Such authentication of persons by means of biometric data can be used for example in the case of automated teller machines, mobile phones, and computers.

Prior art sensor devices of this type are usually produced by the sensor chip being mounted on a mounting board, the terminal pads of the sensor chip subsequently being connected to the conductor tracks on the mounting board by means of a wire bonding method and the sensor chip being encapsulated in a composition in order to keep it stable on the mounting board and protect it. Such a configuration is known, for example, from French published patent application FR 2 736 179 A1. There, it is disadvantageous, however, that such a configuration entails a relatively complex production process. Furthermore, the mounting of such a sensor device in the receiving housing is often relatively complicated and tolerance-critical.

Another prior art sensor device is known from European published patent application EP 0 786 745 A2. There, a housing surrounding the sensor chip is formed from a plastic encapsulating composition in such a way that the sensor surface is accessible via an opening in the housing. Furthermore, the international publication WO 98/11500 describes a sensor device in which the sensor is made up of thin metal layers around a flexible plastic substrate.

Conductor tracks on the plastic substrate establish a connection between the sensor and a terminal region of the flexible plastic substrate. However, the construction of the sensor device described in WO 98/11500 is complicated and difficult to fit into different appliances.

SUMMARY OF THE INVENTION

The object of the invention is to provide a sensor device for detecting biometric characteristics, such as finger minutiae, which overcomes the above-noted deficiencies and disadvantages of the prior art devices and methods of this kind, and wherein the sensor device can be produced particularly simply and, in addition, can be fitted into appliances in a simple way.

With the above and other objects in view there is provided, in accordance with the invention, a sensor device for sensing biometric characteristics, comprising:

a terminal region;

a flexible circuit board having a highly flexible substrate layer, a plurality of conductor tracks on the substrate layer leading to the terminal region, and a grounding conductor track;

the flexible circuit board having formed therein a through-opening and an electrically conducting grounding frame at least partially surrounding the through-opening on a contact side of the sensor device and being electrically connected with the grounding conductor track of the flexible printed circuit board;

a biometric sensor chip mounted on the flexible printed circuit board and electrically connected to the conductor tracks; and the sensor chip having a sensor zone, for example for sensing finger minutiae, accessible on the contact side of the sensor device through the through-opening in the flexible printed circuit board.

In accordance with an additional feature of the invention, the conductor tracks are arranged on an underside of the flexible circuit board, and sensor chip pads on an upper side of the sensor chip are electrically connected to the conductor tracks.

In accordance with a concomitant feature of the invention, the highly flexible substrate layer is formed of Kapton® or of a PET film.

In other words, the sensor chip is fastened on a flexible printed circuit board which comprises a highly flexible substrate material and conductor tracks which have been applied to the substrate material, are in electrical contact with the sensor chip and are led to a terminal region of the flexible printed circuit board.

The sensor device according to the invention offers the advantage that the sensor chips can be mounted and tested on flexible printed circuit boards which are in the form of endless strips or repeats, i.e. relatively large sheets on which there are a plurality of flexible printed circuit boards. The fitting of the sensor devices into the appliances is easy to integrate into the production process and is accordingly inexpensive. The connection between the terminal region of the flexible printed circuit board and the appliance can take place via a standard plug-in connection, for example a zero-insertion-force connector, or a soldered connection. Furthermore, the flexible printed circuit board can be customized, i.e. the length, width, shape of the terminals etc. of the flexible printed circuit board can be designed individually in a simple way. On account of the flexibility of the flexible printed circuit board, the sensor device is also easy to mount when there are relatively great tolerances in the height of the receiving space of the appliance.

The sensor chip is in this case fastened on the flexible printed circuit board in such a way that the sensor zone of the sensor chip is accessible through a through-opening in the flexible printed circuit board. The through-opening in the flexible printed circuit board is surrounded on the contact side at least partially by an electrically conducting grounding frame which is in electrically conducting connection with a conductor track of the flexible printed circuit board. When a finger is placed onto the sensor device, for example, such a grounding frame is inevitably brought into electrical contact by the finger and discharges voltage peaks from the finger to the ground. Such a grounding frame can be applied very simply and in the same way as the conductor tracks to the flexible substrate material of the flexible printed circuit board.

In accordance with an added feature of the invention, a dimensionally stable holding and guiding part is provided and formed with a depression configured to receive therein the sensor chip. The sensor chip is fixed in the depression. Such a holding and guiding part serves for the fastening of the entire sensor device on the appliance, positions the sensor chip by means of the depression and at the same time protects the sensor chip, since the latter is embedded in the depression.

Since the sensor chip is fastened from the underside of the flexible printed circuit board on the latter, it is expedient if the sensor pads, i.e. its terminal contacts, are arranged on the upper side of the sensor chip, so that conductor tracks arranged on the underside of the flexible printed circuit board can be placed directly onto the sensor chip pads and electrically connected to them. This electrical connection may be carried out by known methods such as heat sealing, soldering, thermocompression or thermosonic bonding, wire bonding etc. It is also readily possible, however, to apply the conductor tracks of the flexible printed circuit board additionally or alternatively to the upper side of the substrate layer and bring them into electrical contact through an opening through the substrate layer and the sensor pads.

Other features which are considered as characteristic for the invention are set forth in the appended claims.

Although the invention is illustrated and described herein as embodied in a sensor device for sensing biometric characteristics, in particular finger minutiae, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
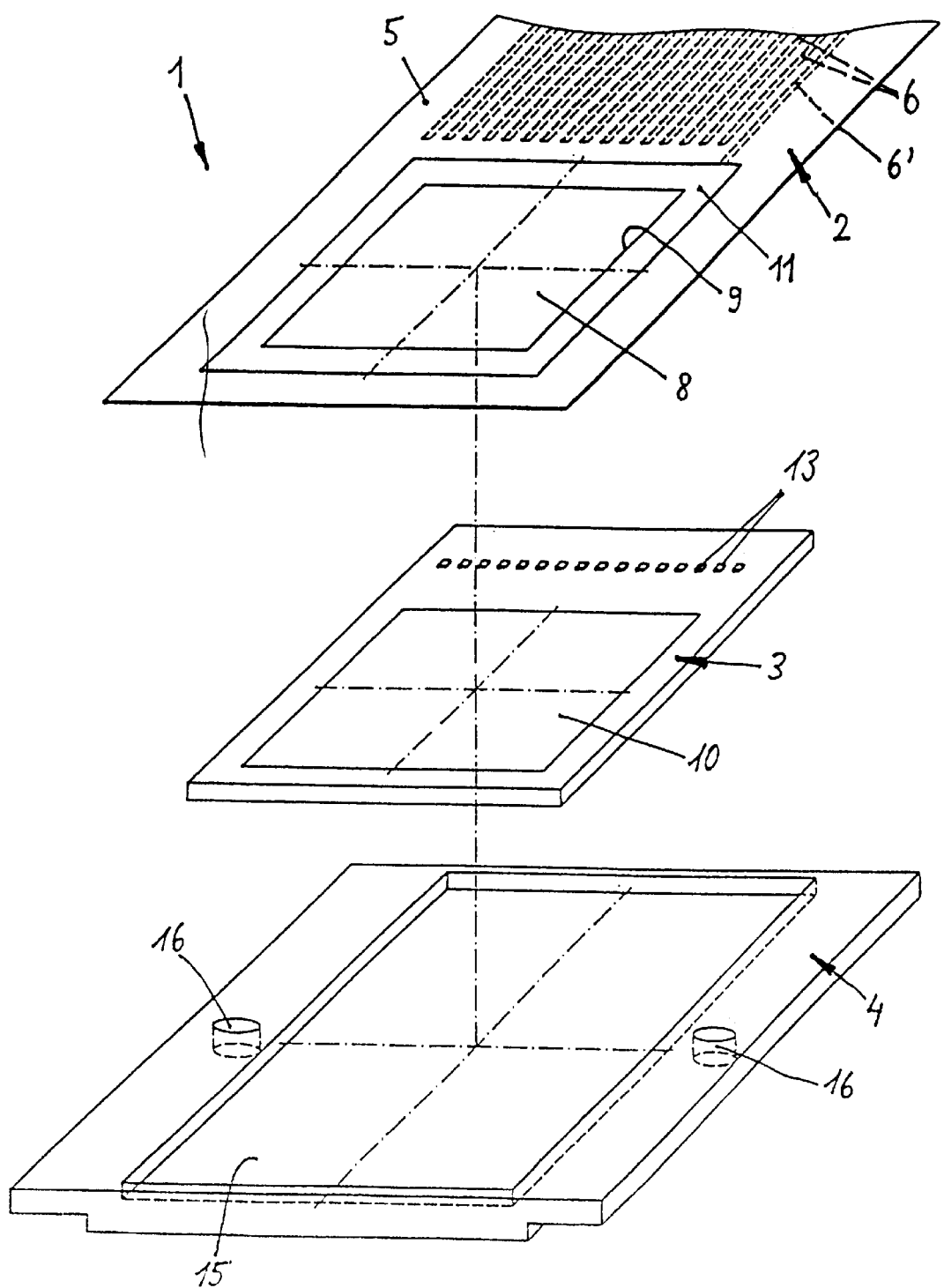
FIG. 1 is an exploded perspective representation of the sensor device according to the invention, with a flexible printed circuit board, sensor chip, and holding and guiding part.

Referring now to the figures of the drawing in detail and first, particularly, to FIG. 1 thereof, there is seen a sensor device 1, represented in exploded view. The sensor device 1 essentially comprises a flexible printed circuit board 2, a sensor chip 3, and a holding and guiding part 4.

Figure 2:
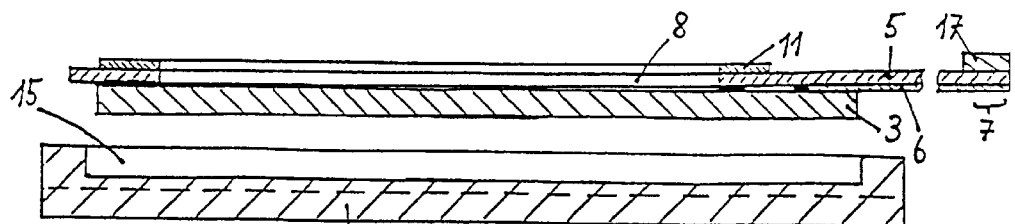
FIG. 2 is a longitudinal section through the sensor device illustrated in FIG. 1 before the sensor chip is placed into the holding and guiding part.
Figure 3:
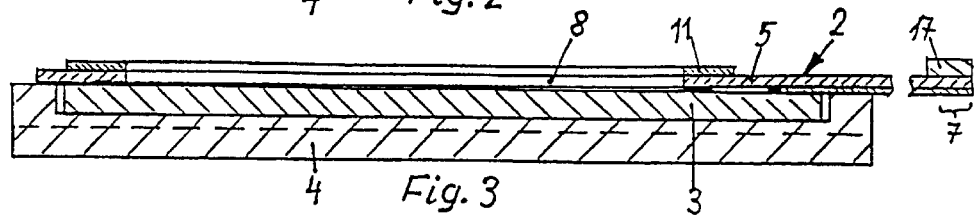
FIG. 3 is a similar section as FIG. 2 after the placement of the sensor chip.
Figure 4:
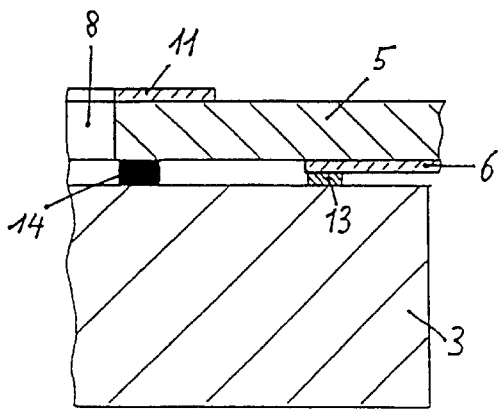
FIG. 4 is a partial longitudinal section taken along the line IV—IV in FIG. 6 with the sensor chip mounted.

The flexible printed circuit board 2 comprises a thin, highly flexible, non-conducting substrate layer 5, for example of Kapton® (E. I. Du Pont De Nemours) or a PET film (polyethylene terephthalate). Applied to the underside of this substrate layer 5 are a multiplicity of conductor tracks 6, which in the case of the illustrated exemplary embodiment extend essentially in the longitudinal direction of the strip-like flexible printed circuit board 2 from a terminal region 7 (see FIGS. 2 and 3), which is located at one end of the flexible printed circuit board 2, in the direction of a rectangular (or square) through-opening 8. The edge of this through-opening 8 is provided with the reference numeral 9 in FIGS. 1 and 6. The size of the through-opening 8 corresponds approximately to the size of a sensor zone 10 of the sensor chip 3. Here, that sensitive area of the sensor chip 3 which can sense the minutiae of a finger placed on the sensor zone 10 is referred to as the sensor zone 10.

Figure 5:
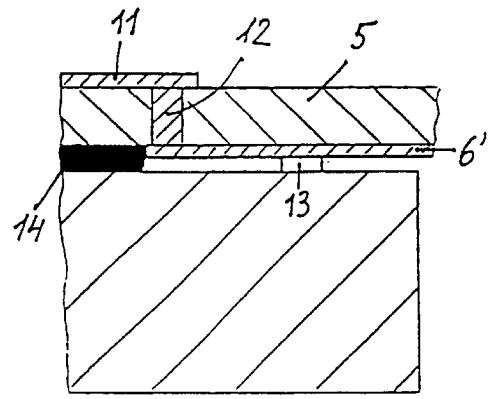
FIG. 5 is a partial longitudinal section taken along the line V—V in FIG. 6 with the sensor chip mounted.

Applied to the substrate layer 5 on the upper side of the flexible printed circuit board 2, i.e. to the side of the substrate layer 5 lying opposite the conductor tracks 6, is a grounding frame 11 which completely surrounds the through-opening 8 at its edge 9. The grounding frame 11 is formed of an electrically conducting material, so that, when there is contact with a finger, voltage peaks present there can be discharged. For this purpose, the grounding frame 11 is electrically connected via a plated-through hole 12 (FIG. 5), passing through the substrate layer 5, to a grounding conductor track 6', which is located on the underside of the flexible printed circuit board 2 in the same way as the conductor tracks 6.

The conductor tracks 6, the grounding conductor track 6' and the grounding frame 11 are produced by applying a copper foil or silver conductive paste to the substrate layer 5. Subsequently, they are suitably structured by etching and provided with a suitable metallization, for example of SnPb or NiAu, in order to prevent oxidation.

Figure 6:
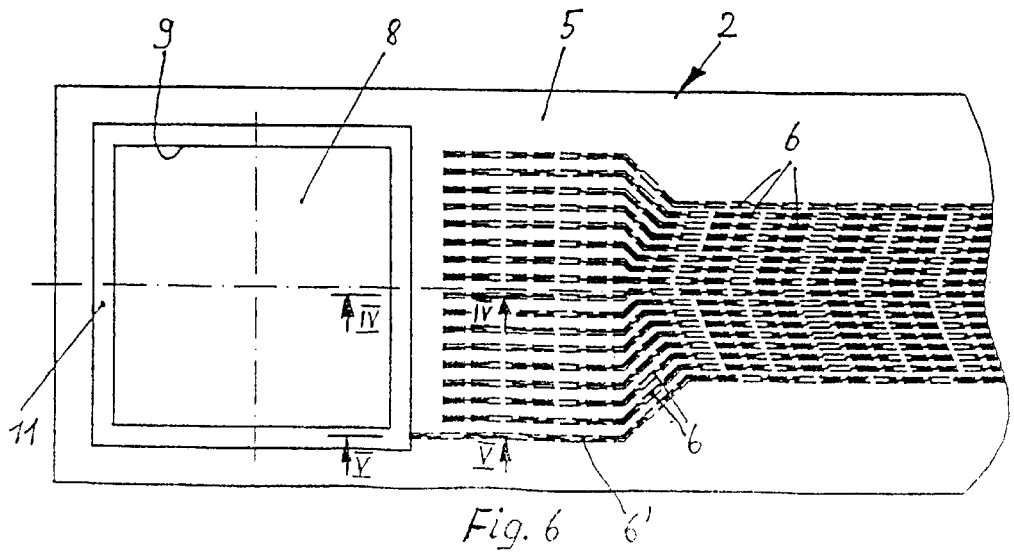
FIG. 6 is a plan view onto the flexible printed circuit board.

As illustrated further in FIG. 6, the conductor tracks 6 do not extend right up to the grounding frame 11 in the longitudinal direction but end shortly before it. The grounding conductor track 6', on the other hand, extends in the longitudinal direction to under the grounding frame 11, so that one vertical plated-through hole 12 is sufficient to establish the electrical connection between the grounding frame 11 and the grounding conductor track 6'.

The sensor chip 3 has exposed pads 13 (terminal contacts) on its upper side. The pads 13 are arranged at a certain distance ahead of the sensor zone 10 in such a way that each pad 13 is in contact with an assigned conductor track 6 if the sensor chip 3 is fastened from below in the predetermined way on the flexible printed circuit board 2. The fixing of the sensor chip 3 on the flexible printed circuit board 2 takes place by means of an adhesive 14, which is applied next to the edge 9 of the through-opening 8. The sensor chip 3 is mounted here on the flexible printed circuit board 2 in such a way that the sensor zone 10 is aligned with respect to the through-opening 8. The sensor zone 10 points upward in the mounted state, so that it can be brought into electrical contact by the finger through the through-opening 8.

The sensor chip 3 mounted on the flexible printed circuit board 2 is subsequently placed into a depression 15 of the holding and guiding part 4 and fixed therein, for example by adhesive bonding. The depression 15 is adapted to the outer contour of the sensor chip 3 in such a way that the sensor chip 3 is placed into the depression 15 only with a small clearance, so that exact guidance and positioning is ensured for the sensor chip 3. The depth of the depression 15 is dimensioned such that the sensor chip 3 is essentially embedded completely, i.e., in the placed-in state, the surface of the sensor chip 3 is flush with the laterally adjacent surface of the holding and guiding part 4. The mechanical stability of the sensor chip 3 is consequently achieved on the one hand by a relatively large chip thickness and on the other hand by the fitting of the sensor chip 3 into the holding and guiding part 4, which consists of a correspondingly flexurally resistant material.

The plate-like holding and guiding part 4 is furthermore formed with vertical holes 16 in the side regions, which serve either as screw holes for fastening the sensor device 1 on a housing or as positioning aids to allow the sensor device 1 to be fitted onto correspondingly protruding domes of the housing.

As an alternative to the embodiment described, it is readily possible to form the conductor tracks 6 additionally or alternatively on the upper side of the substrate layer 5. In this case, the substrate layer 5 has corresponding openings to allow the pads 13 to be connected, for example by means of the wire bonding method, to the conductor tracks located on the upper side of the substrate layer 5.

The conductor tracks 6 and the grounding conductor track 6' may end in the region of the terminal region 7 in a standard plug-in connection, for example a zero-insertion-force connector, which is not represented. In that region, the flexible printed circuit board 2 is secured against being mechanically bent too easily by a transverse reinforcing strip 17. Instead of a plug-in connection, corresponding soldered connections may also be readily carried out in this end region.

The length of the flexible printed circuit board 2 is only represented in a shortened form in FIGS. 1 to 6. As can be seen, the length of the flexible printed circuit board 2 can be adapted in a simple way to the individual fitting requirements and customer wishes. For example, the length of the flexible printed circuit board 2 may be 1.5 to any times the length of the sensor chip 3.

It will be understood that the dimensions, in particular the relative thicknesses of the individual components, are not drawn true to scale for reasons of a clearer representation.

We claim:

1. A sensor device for sensing biometric characteristics, comprising:
   a terminal region;
   a flexible circuit board having a highly flexible substrate layer, a plurality of conductor tracks applied to said substrate layer and leading to said terminal region, and a grounding conductor track;
   said flexible circuit board having formed therein a through-opening and an electrically conducting grounding frame at least partially surrounding said through-opening on a contact side of the sensor device and being electrically connected with said grounding conductor track of the flexible printed circuit board;
   a biometric sensor chip mounted on said flexible printed circuit board and electrically connected to said conductor tracks;
   said sensor chip having a sensor zone accessible on the contact side of the sensor device through said through-opening in said flexible printed circuit board.

2. The sensor device according to claim 1, wherein said sensor zone of said sensor chip is configured to sense finger minutiae.

3. The sensor device according to claim 1, which comprises a dimensionally stable holding and guiding part formed with a depression configured to receive therein and fix said sensor chip.

4. The sensor device according to claim 1, wherein said conductor tracks are arranged on an underside of said flexible printed circuit board, and said sensor chip includes sensor chip pads on an upper side thereof and electrically connected to said conductor tracks.

5. The sensor device according to claim 1, wherein said substrate layer of said flexible printed circuit board is formed of Kapton® material.

6. The sensor device according to claim 1, wherein said substrate layer of said flexible printed circuit board is formed of a PET film.

\* \* \* \* \*

UNITED STATES PATENT AND TRADEMARK OFFICE
CERTIFICATE OF CORRECTION

PATENT NO. : 6,347,040 B1
DATED : February 12, 2002
INVENTOR(S) : Manfred Fries et al.

It is certified that error appears in the above-identified patent and that said Letters Patent is hereby corrected as shown below:

<u>Title page,</u>
Item [75], should read as follows:

-- Manfred Fries, Hunderdorf; Reinhard Fischbach, München; Detlef Houdeau, Langquaid, all of (DE) --

Signed and Sealed this

Twentieth Day of August, 2002

*Attest:*

*Attesting Officer*

JAMES E. ROGAN
*Director of the United States Patent and Trademark Office*